(12) United States Patent
Shah et al.

(10) Patent No.: US 11,826,429 B2
(45) Date of Patent: *Nov. 28, 2023

(54) PHARMACEUTICAL COMPOSITION COMPRISING BRINZOLAMIDE

(71) Applicant: SENTISS PHARMA PRIVATE LIMITED, New Delhi (IN)

(72) Inventors: Mandar V. Shah, New Delhi (IN); Deepak Bahri, New Delhi (IN)

(73) Assignee: SENTISS PHARMA PRIVATE LIMITED, New Delhi (IN)

( * ) Notice: Subject to any disclaimer, the term of this patent is extended or adjusted under 35 U.S.C. 154(b) by 719 days.

This patent is subject to a terminal disclaimer.

(21) Appl. No.: 16/811,674

(22) Filed: Mar. 6, 2020

(65) Prior Publication Data

US 2020/0197522 A1 Jun. 25, 2020

Related U.S. Application Data

(63) Continuation of application No. 15/112,274, filed as application No. PCT/IB2015/050511 on Jan. 23, 2015, now Pat. No. 10,632,198.

(30) Foreign Application Priority Data

Jan. 24, 2014 (IN) .............................. 223/DEL/2014

(51) Int. Cl.
| | | |
|---|---|---|
| *A61K 47/34* | (2017.01) | |
| *A61K 9/00* | (2006.01) | |
| *A61K 47/26* | (2006.01) | |
| *A61K 31/542* | (2006.01) | |
| *A61K 9/08* | (2006.01) | |
| *A61K 47/32* | (2006.01) | |

(52) U.S. Cl.
CPC ............ *A61K 47/34* (2013.01); *A61K 9/0048* (2013.01); *A61K 9/08* (2013.01); *A61K 31/542* (2013.01); *A61K 47/26* (2013.01); *A61K 47/32* (2013.01)

(58) Field of Classification Search
CPC ........ A61K 47/34; A61K 9/0048; A61K 9/08; A61K 31/542; A61K 47/26; A61K 47/32
See application file for complete search history.

(56) References Cited

U.S. PATENT DOCUMENTS

| | | |
|---|---|---|
| 5,378,703 A | 1/1995 | Dean et al. |
| 6,071,904 A | 6/2000 | Ali et al. |
| 2013/0023536 A1* | 1/2013 | Graham ................. A61K 47/38 514/249 |

FOREIGN PATENT DOCUMENTS

| | | |
|---|---|---|
| WO | WO-98/25620 A1 | 6/1998 |
| WO | WO-2011/067791 A2 | 6/2011 |
| WO | WO-2013/090842 A2 | 6/2013 |
| WO | WO-2013/175285 A1 | 11/2013 |

* cited by examiner

*Primary Examiner* — Genevieve S Alley
(74) *Attorney, Agent, or Firm* — Foley & Lardner LLP (57) ABSTRACT

A sterile aqueous formulation of a carbonic anhydrase inhibitor such as brinzolamide in combination with polymers like Soluplus® and a surfactant like polysorbate 80, as well as methods of preparation thereof, is disclosed. The formulation relates to the highly solubilized or an amorphous form of poorly insoluble drugs/active ingredient(s) to improve its bio-availability and manufacturability.

25 Claims, 6 Drawing Sheets

PHARMACEUTICAL COMPOSITION COMPRISING BRINZOLAMIDE

CROSS-REFERENCE TO RELATED APPLICATIONS

The present application is the Continuation of U.S. patent application Ser. No. 15/112,274, filed on Jul. 18, 2016, which is a U.S. National Phase of International Patent Application No. PCT/IB2015/050511, filed Jan. 23, 2015, which claims priority to Indian Patent Application No. 223/DEL/2014, filed Jan. 24, 2014, the entireties of which are incorporated herein by reference.

FIELD OF THE INVENTION

The present invention relates to the highly solubilized or an amorphous form of poorly insoluble drugs/active ingredient(s) to improve its bio-availability and manufacturability.

The present invention relates to pharmaceutical composition comprising of the stabilized amorphous form of poorly insoluble drugs/active ingredient(s) which resulted in significantly enhanced bioavailability over the crystalline form of the compound, currently marketed as a suspension product.

The present invention relates to sterile, ophthalmic pharmaceutical formulation comprising active ingredient(s) such as carbonic anhydrase inhibitors (CAIs) like brinzolamide and/or other pharmaceutically acceptable excipients.

BACKGROUND OF THE INVENTION

Brinzolamide is a carbonic anhydrase inhibitor used to lower intraocular pressure in patients with ocular hypertension or open-angle glaucoma. Brinzolamide is chemically (R)-(+)-4-ethylamino-2-(3-methoxypropyl)-3,4-dihydro-2H-thieno[3,2-e]-1,2-thiazine-6-sulfonamide-1, 1-dioxide and has the empirical formula $C_{12}H_{21}N_3O_5S_3$. Brinzolamide has a molecular weight of 383.5 and a melting point of about 131° C.

This compound is disclosed in U.S. Pat. No. 5,378,703 (Dean, et al). The compound is also disclosed in European patent EP 527801. U.S. Pat. No. 6,071,904 discloses processes for preparation of brinzolamide ophthalmic composition.

Brinzolamide in the form of ophthalmic suspension is developed and marketed by Alcon Laboratories Inc. in United States under the brand name Azopt® (brinzolamide ophthalmic suspension 1%). Brinzolamide is indicated for lowering elevated intra-ocular pressure (IOP) in patients with open-angle glaucoma or ocular hypertension (OHT).

Various methods have been disclosed in the prior art for the preparation of brinzolamide ophthalmic suspension. International patent application WO 98/25620 teaches that conventional sterilization methods cannot be employed in the manufacture of suspensions comprising brinzolamide since the compound recrystallizes as large needle-shaped crystals, upon cooling, after autoclaving.

According to WO 98/25620, dry heat sterilization is also not suitable, since it causes melting of the material, whereas sterilization by ethylene oxide and gamma irradiation introduces unacceptable degradation products.

EP0941094 discloses a process for making brinzolamide suspension by autoclaving of concentrated slurry of brinzolamide and tyloxapol; or brinzolamide and Triton X in milling bottle, and ball milling of the hot slurry after autoclaving, and then adding the slurry to the rest of the ingredients. It should be noted here that high temperatures and pressures of autoclave will dissolve brinzolamide. Later, when autoclaving is complete, upon cooling brinzolamide precipitates as large shaped crystals, having particle size of 1000 to 5000 µm. However, inclusion of tyloxapol and/or Triton X in the slurry allows the crystals to break up easily by ball milling. Brinzolamide cannot be administered as these large needle shaped crystals, as they will damage the eyes. Hence, precipitated brinzolamide crystals need to be milled to reduce their particle size.

Thus, the reference discloses autoclaving of the slurry of brinzolamide and surfactant and further ball milling the slurry. However, the drawback associated with this method is that it requires a milling bottle in which the slurry of brinzolamide could initially be autoclaved and then ball milled for further size reduction of needle shaped crystals of brinzolamide that are formed during autoclaving.

Dry heat sterilization causes melting of the material. Sterilization by ethylene oxide introduces unacceptable degradation products and residues, and sterilization by gamma irradiation of micronized material produces degradation products unacceptable for regulatory filing.

In most cases crystallization of active ingredients useful for ophthalmic use like carbonic anhydrase inhibitor, or others actives, occurs during preparation. Sterilization by autoclaving at temperature of 121° C. and 115 lbs of pressure leads to increase in solubility of the actives in the preparation and at that temperature brinzolamide goes into solution. However, upon cooling, brinzolamide precipitates as needle shaped crystals. These needle-shaped crystals are difficult to break and suspend. In different references either tyloxapol is used in solution so that the crystals are easier to break or special equipment such as ball mill and/or jet mill is used to break the large needle-shaped crystals.

The majority of the suspensions disclosed in the references faced the problem of crystallization and agglomeration of active ingredients during preparation as well as during storage. Crystallization or agglomeration of active leads to non-uniformity of dose, difficulty of administration, irritation to eye due to large drug particles and/or any ocular adverse effect due to high drug concentration.

So, there remains a need to formulate a dosage form in which drugs like brinzolamide, having low solubility can be solubilized or the drug is present in an amorphous form, to increase the permeability and bioavailability of the drug. None of the prior art disclosed above teaches about increased solubility of brinzolamide or converting it in an amorphous form.

The inventors of the present invention has formulated a sterile, ophthalmic pharmaceutical formulation, wherein when the active ingredient with low aqueous solubility (such as brinzolamide) in combination with polymers like Soluplus® and a surfactant like polysorbate 80, is either autoclaved or dissolved after heating above 50° C. Upon cooling, the active ingredient brinzolamide does not precipitate and stays in solution or in a partially amorphous form.

OBJECTS OF THE PRESENT INVENTION

The main object of the present invention is to provide an aqueous sterile, ophthalmic pharmaceutical formulation comprising carbonic anhydrase inhibitor, amphiphilic polymer and surfactant.

Yet another object of the present invention is to provide an ophthalmic pharmaceutical formulation which optionally contains pharmaceutically acceptable excipients.

Yet another object of the present invention is to provide an ophthalmic pharmaceutical formulation wherein the formulation is in the form of an aqueous solution.

Yet another object of the present invention is to provide an ophthalmic pharmaceutical formulation wherein the formulation comprises less than 1% w/v of carbonic anhydrase inhibitor.

Yet another object of the present invention is to provide an ophthalmic pharmaceutical formulation with improved bio-availability and manufacturability.

Yet another object of the present invention is to provide a process for manufacturing ophthalmic pharmaceutical formulation without use of any equipment such as ball mill and/or, jet mill.

Yet another object of the present invention is to provide a sterile ophthalmic pharmaceutical formulation that is useful in the treatment of elevated intraocular pressure.

SUMMARY OF THE INVENTION

The present invention is to formulate a sterile, ophthalmic pharmaceutical formulation, wherein the poorly soluble drug/active ingredient such as carbonic anhydrase inhibitors (CAIs), solubilizes during either cooling after autoclaving or cooling after heating above 50° C. in a partially amorphous form.

The present invention further relates to sterile, ophthalmic pharmaceutical formulation comprising active ingredient(s) such as carbonic anhydrase inhibitors (CAIs) like brinzolamide in combination with a polymer like Soluplus® and a surfactant like polysorbate 80 and/or other pharmaceutically acceptable excipients.

The present invention furthermore relates to the highly solubilized or an amorphous form of poorly insoluble drugs/active ingredient(s) to improve its bio-availability and manufacturability.

The present invention additionally relates to pharmaceutical composition comprising of the stabilized amorphous form of poorly insoluble drugs/active ingredient(s) which resulted in significantly enhanced dissolution and bioavailability over the crystalline form of the compound.

The present invention further provides a process of preparing a sterile, ophthalmic pharmaceutical formulation, wherein during either cooling after autoclaving or cooling after heating above 50° C. the active ingredient brinzolamide does not precipitate and it turns into partially amorphous and/or in a solubilized form. It is believed that the amorphous or a solubilized form of a drug, increases bio-availability compared to a crystalline component, such that there should be a reduction in therapeutically effective dose of brinzolamide.

The present invention further relates to provide a process, wherein the amorphous or a solubilized brinzolamide as a part, is formed by the use of ophthalmically acceptable ingredients such as polymers like Soluplus® {polyvinyl caprolactam-polyvinyl acetate-polyethylene glycol graft copolymer (PVCap-PVAc-PEG)} and surfactants like polysorbate 80 (Polyoxyethylene (20) sorbitan monooleate), or a combination of these ingredient(s).

This present invention additionally provides a process for preparation of a formulation, that is efficient, economical, and feasible for commercial scale preparation and wherein the process does not require the use of equipments such as ball mill and/or jet mill.

Further, the invention provides a process which ameliorates one or more drawbacks of the reference cited processes.

The sterile, ophthalmic pharmaceutical brinzolamide formulation as prepared in the present invention are useful in the treatment of conditions treatable with brinzolamide, e.g., elevated intraocular pressure in persons suffering from ocular hypertension or primary open angle glaucoma.

DETAILED DESCRIPTION OF THE INVENTION

As used herein, the term "Soluplus®" wherever appears is an amphiphilic polyvinyl caprolactam-polyvinyl acetate-polyethylene glycol graft copolymer (PVCap-PVAc-PEG).

As used herein, the term "API" wherever appears is an abbreviation for "brinzolamide".

As used herein, the term "commercial product" wherever appears is the U.S. FDA approved product "AZOPT".

As used herein, the term "NMT" wherever appears is an abbreviation for "not more than".

As used herein, the term "BDL" wherever appears is an abbreviation for "below detection limit".

As used herein, the term "ND" wherever appears is an abbreviation for "None detected".

As used herein, wherever the drug comprises brinzolamide, the impurities preferably measured include Impurity A as (S)-4-(ethylamino)-3,4-dihydro-2-(3-methoxypropyl)-2H-thieno[3,2-e]-1,2-thiazine-6-sulfonamide 1,1-dioxide; Impurity B as (R)-4-(amino)-3,4-dihydro-2-(3-methoxypropyl)-2H-thieno[3,2-e]-1,2-thiazine-6-sulfonamide 1,1-dioxide; Impurity C as (S)-4-(hydroxy)-3,4-dihydro-2-(3-methoxypropyl)-2H-thieno[3,2-e]-1,2-thiazine-6-sulfonamide 1,1-dioxide and Impurity D as 6-(amino-hydroxy-oxo-6-sulfanyl)-2-(3-methoxypropyl)-1,1-dioxo-3H-thieno[3,2-e]thiazin-4-one.

As used herein, the term "poorly soluble" when referring to a chemical compound in relation to its solubility in water or an oil, as defined in U.S. Pharmacopeia and National Formulary (USP-NF). According to this definition, solubility is stated in terms of the parts of the solvent needed to dissolve one part of the solute. A compound that is sparingly soluble in a particular solvent, such as water, requires 30-100 parts of the solvent to dissolve one part of the compound. A compound that is slightly soluble requires 100-1000 parts of the solvent. A compound that is very slightly soluble requires 1000-10,000 parts of the solvent. A compound that is insoluble requires more than 10,000 parts of the solvent to dissolve one part of the solute.

The present invention is to formulate a sterile, ophthalmic pharmaceutical formulation, wherein the poorly soluble drug/active ingredient such as carbonic anhydrase inhibitors (CAIs), solubilizes during either cooling after autoclaving or cooling after heating above 50° C. in a partially amorphous form.

The present invention further relates to sterile, ophthalmic pharmaceutical formulation comprising active ingredient(s) such as carbonic anhydrase inhibitors (CAIs) like brinzolamide in combination with a polymer like Soluplus® and a surfactant like polysorbate 80 and/or other pharmaceutically acceptable excipients.

The present invention furthermore relates to the highly solubilized or an amorphous form of poorly insoluble drugs/active ingredient(s) to improve its bio-availability and manufacturability.

The present invention additionally relates to pharmaceutical composition comprising of the stabilized amorphous form of poorly insoluble drugs/active ingredient(s) which resulted in significantly enhanced dissolution and bioavailability over the crystalline form of the compound.

The present invention further provides a process of preparing a sterile, ophthalmic pharmaceutical formulation, wherein during cooling, brinzolamide does not precipitate and turns into partially amorphous form or a solubilized form, so that there is a reduction in therapeutically effective dose of brinzolamide. It is believed that the amorphous component increases bioavailability compared to a crystalline component, such that there should be a reduction in therapeutically effective dose of brinzolamide.

The present invention further relates to provide a process, wherein the solubilized amorphous brinzolamide as a part, is formed by the use of ophthalmically acceptable ingredients such as polymers like Soluplus®, and surfactants like polysorbate 80, or a combination of these ingredient(s).

Another embodiment of the present invention is to provide a sterile, ophthalmic pharmaceutical solution and process of making said solution, which comprising active ingredient(s) such as carbonic anhydrase inhibitors (CAIs) like brinzolamide, wherein the process does not require the use of specific equipment's such as ball mill and/or jet mill.

This present invention additionally provides a process for preparation of a formulation, the process being efficient, economic, and feasible for commercial scale preparation and wherein the process does not require the use of specific equipments such as ball mill and/or jet mill.

Further, in one aspect of the present invention, the inventors of the present invention have conducted extensive studies and add ophthalmically acceptable ingredients such as polymers like Soluplus® or surfactants like polysorbate 80 or combination of these ingredients.

In a preferred embodiment of the present invention, there is provided a sterile, ophthalmic pharmaceutical formulation prepared by the process as described herein comprising brinzolamide in an amount from about 0.01% to 5.0% by weight and/or pharmaceutically acceptable excipients.

According to one embodiment, the present invention relates to provide a sterile, ophthalmic pharmaceutical formulation and process of making such formulation comprising active ingredient(s) such as carbonic anhydrase inhibitors (CAIs) like brinzolamide, wherein the process does not require the use of specific equipment's such as ball mill and/or jet mill.

In one of the aspect of the present invention, the inventors of the present invention have conducted extensive studies and added innocuous ingredients such as polymers like Soluplus® or surfactant like polysorbate 80 or combination of these ingredients that will alter the crystal formation of brinzolamide, when it is either cooled after autoclaving or cooled after heating above 50° C., into partially amorphous form or a solubilized form.

In one of the embodiment, the present invention provides a process for preparation of sterile, brinzolamide ophthalmic formulation, the process being efficient, economic, and feasible for commercial scale preparation and which does not require the use of any special equipment's such as ball mill and/or jet mill.

The sterile, ophthalmic pharmaceutical brinzolamide formulation as prepared in the present invention are useful in the treatment of conditions treatable with brinzolamide, e.g., elevated intraocular pressure in persons suffering from ocular hypertension or primary open angle glaucoma.

Another embodiment of the present invention is to provide a process which ameliorates one or more drawbacks of the reference cited processes.

According to one embodiment of the present invention, there is provided a sterile ophthalmic formulation prepared by the process as described herein comprising brinzolamide in an amount from 0.01% to 5.0% by weight.

In preferred embodiments, the present invention provides sterile ophthalmic formulations in the form of aqueous liquids, solutions, emulsion, solid dispersion, suspension, reverse emulsion and microemulsion, nanoemulsion, nano reservoir system, in-situ gel drops, nanoparticulate system, liposomal drops, bioadhesive gel drops, drops and the like.

In another preferred embodiment, the present invention provides ophthalmic formulations for topical ophthalmic delivery comprising administering said composition in the eyes. Other preferred embodiments include optic and/or nasal formulations for administration to the ear and/or nose of a human or animal.

In a more preferred embodiment of the present invention, the pharmaceutically acceptable excipients are selected from but not limited to at least one polymer, at least one surfactant, at least one isotonicity agent, at least one viscosity enhancing agent, at least one solvent, at least one buffer, at least one pH adjusting agents, at least one antioxidants, at least one chelating agents and at least one preservative.

In one of the embodiments, the polymers that may be used is selected from the group consisted of, but are not limited to Carbomer® such as Carbomer 974 P, an amphiphilic polymer such as Soluplus® (polyvinyl caprolactam-polyvinyl acetate-polyethylene glycol graft copolymer), povidone, hydroxypropylmethylcellulose, hydroxypropylcellulose, hydroxyethylcellulose and mixtures thereof, wherein the said polymers may be used in amount from 0.01% to 5.0%.

In one of the embodiments, the preservatives that may be used is selected from the group consisted of, but are not limited to benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, benzoic acid, benzyl alcohol, butylparaben, propylparaben, methylparaben, chlorobutanol, phenoxyethanol, sodium methyl paraben, sodium propyl paraben, thimerosal, benzalkonium chloride, hydrogen peroxide, sodium chlorite and mixtures thereof, wherein the said preservatives may be used in an amount from 0.005% to 0.5%.

In another embodiment, the surfactants that may be used is selected from the group consisted of, but are not limited to sodium lauryl sulfate, docusate sodium, polyoxyalkyl ethers, polyoxyalkyl phenyl ethers, polyoxyl 40 hydrogenated castor oil (Cremophor RH 40), polyoxyl 40 stearates, polyoxy hydrogenated castor oil, tyloxapol, polyoxy sorbitan esters, sorbitan esters, polysorbates such as polysorbate 80, polyoxyl 35 castor oil, sorbitan monolaureates, poloxamer and mixtures thereof, wherein the said surfactants may be used in amount from 0.001% to 15%, preferably 0.01% to 5.0%.

In one of the embodiments, the tonicity or osmotic agents that may be used is selected from the group consisted of, but are not limited to mannitol, dextrose, glycerin, potassium chloride, sodium chloride and mixtures thereof, wherein the tonicity agents may be used in amount from about 0.1% to 5.0% or is added in such an amount that makes the osmotic pressure of the composition identical to that of tears.

In other embodiments, the solvent, preferably a polar organic solvent, is selected from the group consisting of, but not limited to N-methyl pyrrolidinone, aliphatic and aromatic alcohols, ethanol, dimethyl sulfoxide (DMSO), dimethyl acetamide, ethoxydiglycol, isopropyl myristate, triacetin, polyethylene glycols, and propylene glycol.

In another embodiment, the viscosity enhancing agents that may be used is selected from the group comprising of, but are not limited to, carboxymethylcellulose sodium, hydroxyethyl cellulose, hydroxypropyl cellulose, hydroxymethyl cellulose, hydroxypropyl methylcellulose, methylcellulose carbomer, poloxamer, polyvinyl alcohol, povidone, polyethylene oxide, carboxymethylcellulose calcium.

In one of the preferred embodiment, the active ingredient used in the sterile, ophthalmic pharmaceutical formulation is a carbonic anhydrase inhibitor (CAI). In a preferred embodiment, the carbonic anhydrase inhibitor (CAI) is brinzolamide.

In another embodiment of the present invention, the buffers include acetates such as sodium acetate; phosphates such as sodium dihydrogenphosphate, disodium hydrogenphosphate, potassium dihydrogenphosphate and dipotassium hydrogenphosphate; ε-aminocaproic acid; amino acid salts such as sodium glutamate; and boric acid and a salt thereof, wherein the buffer is generally contained in a proportion of 0.01 to 2.0 w/v % relative to the entire composition.

In another embodiment of the present invention, the buffer should have buffering capacity in the range of pH 4.5-8.5.

In one of another embodiment of the present invention, the pH adjusting agent include but are not limited to, hydrochloric acid, citric acid, phosphoric acid, acetic acid, tartaric acid, sodium hydroxide, potassium hydroxide, sodium carbonate and sodium hydrogencarbonate.

In one of another embodiment of the present invention, the chelating agents include but are not limited to edetate disodium, edetate trisodium, edetate tetrasodium, diethyleneamine pentaacetate and mixtures thereof, wherein the chelating agent is generally present in an amount from 0.005-0.2 w/v % relative to the entire composition.

In one of another embodiment of the present invention, the antioxidants include but are not limited to sodium bisulfite, potassium bisulfite, magnesium bisulfite, calcium bisulfite, sodium metabisulfite, potassium metabisulfite, calcium metabisulfite, sodium thiosulfate and sodium hydrogensulfite, ascorbic acid, sodium ascorbate, tocopherol and sulfite salts like sodium sulfite, potassium sulfite, magnesium sulfite, calcium sulfite, wherein the sulfite salt is generally being present in an amount from 0.01-1.0% w/v.

In one embodiment of the present invention, the solution comprising brinzolamide in a percentage range of from about 0.05% to about 5.0%, polymer in a percentage range of from about 0.01 to about 5.0%, preservative in a percentage range of from about 0.002 to about 0.05%, surfactant in a percentage range of from about 0.01 to about 2.5%, tonicity or osmotic agents in a percentage range of from about 0.01 to about 10.0%, buffer in a percentage range of from about 0.00 to about 2.0%, chelating agent in a percentage range of from about 0.005 to about 1.0%, antioxidant in a percentage range of from about 0.001 to 1.0%.

In one of another embodiment of the present invention, the sterile, ophthalmic pharmaceutical formulation may be aseptically sterilized using membrane filters such as PES (Polyethersulphone), PVDF (Polyvinylidene Fluoride) having pore size of about 0.45 microns to 0.22 microns to filter the formulation vehicle.

In another embodiment of the present invention, the ophthalmic formulation of brinzolamide prepared according to the process as described herein may be filled in LDPE or HDPE or PET or polycarbonate vials of suitable capacity in volumes of 0.5 to 20 mL.

Another embodiment of the present invention consists of the active ingredient which is useful in the treatment or prevention of diseases associated with the eye(s) like elevated intraocular pressure in patients with ocular hypertension or open-angle glaucoma, ocular surface pain, uveitis, scleritis, episcleritis, keratitis, surgically-induced inflammation, endophthalmitis, iritis, atrophic macular degeneration, retinitis pigmentosa, iatrogenic retinopathy, retinal tears, retinal vein and artery occlusion, optic neuropathy, neovascular glaucoma, corneal neovascularization, cyclitis, sickle cell retinopathy, pterygium, seasonal allergic conjunctivitis, palpebral and bulbar conjunctiva, acne rosacea, superficial punctuate keratitis, herpes zoster keratitis, iritis, cyclitis, selected infective conjunctivitides, and post-operative inflammation following ocular surgery.

In another embodiment of the present invention, the active ingredient used in the sterile, ophthalmic pharmaceutical formulation, is selected from the group but are not limited to a carbonic anhydrase inhibitor (CAI), such as brinzolamide, acetazolamide, dorzolamide, methazolamide; non-steroidal anti-inflammatory drugs (NSAID), such as nepafenac, flurbiprofen, diclofenac and ketorolac tromethamine; a prostaglandin analog, such as latanoprost, travoprost, bimatoprost; a steroid, such as fluorometholone, hydrocortisone, dexamethasone, prednisolone, loteprednol, or medrysone and/or other actives used for ophthalmic formulation or a pharmaceutically acceptable salt(s), hydrate(s), solvate(s), polymorph(s), stereoisomers), ester(s), prodrug(s), complex(es) and their metabolites thereof.

The main embodiment of the present invention provides an aqueous sterile, ophthalmic pharmaceutical formulation comprising:
 a) brinzolamide as carbonic anhydrase inhibitor,
 b) an amphiphilic polymer, and
 c) a surfactant,
 and optionally along with pharmaceutically acceptable excipients or their combinations thereof.

In another embodiment of the present invention, the brinzolamide is present in amount from 0.01% to 5.0% by weight of the formulation.

In another embodiment of the present invention, the brinzolamide is present in amount from 0.05% to 3.0% by weight of the formulation.

In another embodiment of the present invention, the brinzolamide is present in amount from 0.1% to 1.0% by weight of the formulation.

In another embodiment of the present invention, the amphiphilic polymer is selected from group comprising carboxyvinyl polymer, polyvinyl caprolactam-polyvinyl acetate-polyethylene glycol graft copolymer, povidone, hydroxypropyl methylcellulose, hydroxypropyl cellulose, or hydroxyethyl cellulose or a combination of two or more thereof.

In another embodiment of the present invention, the amphiphilic polymer is polyvinyl caprolactam-polyvinyl acetate-polyethylene glycol graft copolymer.

In another embodiment of the present invention, the amphiphilic polymer is present in amount from 0.01% to 5.0% by weight of the formulation.

In another embodiment of the present invention, the amphiphilic polymer is present in amount from 0.05% to 3.0% by weight of the formulation.

In another embodiment of the present invention, the amphiphilic polymer is present in amount from 0.1% to 2.0% by weight of the formulation.

In another embodiment of the present invention, the surfactant is selected from group comprising sodium lauryl sulfate, docusate sodium, polyoxyalkyl ether, polyoxylalkyl phenyl ether, polyoxyl 40 hydrogenated castor oil, polyoxyl 40 stearate, polyoxy hydrogenated castor oil, polyoxy sorbitan ester, sorbitan ester, polysorbate, polyoxyl 35 castor oil, sorbitan monolaureate, poloxamer, or a combination of two or more thereof.

In another embodiment of the present invention, the surfactant is polysorbate, preferably polysorbate 80.

In another embodiment of the present invention, the surfactant is present in amount from 0.01% to 5.0% by weight of the formulation.

In another embodiment of the present invention, the surfactant is present in amount from 0.05% to 3.0% by weight of the formulation.

In another embodiment of the present invention, the surfactant is present in amount from 0.1% to 2.0% by weight of the formulation.

In another embodiment of the present invention, the pharmaceutically acceptable excipients are selected from group comprising a tonicity agent, a viscosity enhancing agent, a non-aqueous solvent, a buffer, a pH adjusting agent, an antioxidant, a chelating agent, a preservative, or a combination of two or more thereof.

In another embodiment of the present invention, the carbonic anhydrase inhibitor is present either in dissolved or, amorphous form.

In another embodiment of the present invention, the formulation is in the form of an aqueous solution.

In another embodiment of the present invention, the formulation is in the form of an aqueous suspension.

In another embodiment of the present invention, the formulation does not include any preservative.

In another embodiment of the present invention, the formulation is for topical ophthalmic delivery comprising administering said formulation in the eyes.

In another embodiment of the present invention, the formulation is for topical ophthalmic delivery comprising administering said formulation in the ear and/or nose of a human or animal.

In another embodiment of the present invention, the sterile solution is suitable for ophthalmic use.

In another embodiment of the present invention, the sterile suspension is suitable for ophthalmic use.

In another embodiment of the present invention, the formulation is administered once a day to each eye in need thereof.

In another embodiment of the present invention, the formulation is administered twice a day to each eye in need thereof.

In a preferred embodiment of the present invention, the formulation comprises brinzolamide, polyvinyl caprolactam-polyvinyl acetate-polyethylene glycol graft copolymer, polysorbate 80 and optionally along with pharmaceutically acceptable excipients or their combinations thereof.

Yet another embodiment of the present invention provides a process of preparing an aqueous formulation which comprising the steps of:
 a) preparing a first composition comprising water, an amphiphilic polymer, and a carbonic anhydrase inhibitor;
 b) subjecting the first composition prepared in step (a) to an elevated temperature suitable for sterilization of the composition; and cooling the composition to ambient temperature, to obtain a second composition which is the final product;

wherein the carbonic anhydrase inhibitor in the second composition comprises a dissolved form, or, amorphous form, or both dissolved and amorphous forms.

In yet another embodiment of the present invention, the carbonic anhydrase inhibitor does not precipitate in crystalline form during the cooling of composition.

In yet another embodiment of the present invention, the process does not comprise the use of a ball mill and/or jet mill.

Yet another embodiment of the present invention provides a method of treating elevated intraocular pressure in a patient in need thereof, comprising obtaining a formulation having an effective amount of the carbonic anhydrase inhibitor, and administering an effective amount of the formulation to at least one eye in need thereof of the patient.

In yet another embodiment of the present invention, the formulation comprises less than 1% w/v of carbonic anhydrase inhibitor.

In yet another embodiment of the present invention, the method of reducing an effective dosage of carbonic anhydrase inhibitor for a patient in need thereof, comprising administering to the patient an effective amount of the formulation to at least one eye in need thereof of the patient, the formulation comprising less than 1% w/v of carbonic anhydrase inhibitor.

In yet another embodiment of the present invention, the formulation is administered once a day to each eye in need thereof.

In yet another embodiment of the present invention, the formulation is administered twice a day to each eye in need thereof.

In yet another embodiment of the present invention, the condition treatable includes elevated intraocular pressure.

Following formulations are prepared to carry out DSC measurements.

Methodology:
1. Accurately weigh an appropriate quantity of sample (for brinzolamide the sample quantity taken is about 3 mg) to be examined in a sample pan.
2. The initial temperature, heating rate, and the final temperature for DSC testing of brinzolamide samples are set as:
   Initial temperature: 30° C.,
   Heating Rate: 10° C. per minute
   Final Temperature: 200° C.
3. Provide an inert environment (preferably $N_2$ flow) and then measure the difference in temperature between the sample and reference pan (may differ, e.g., based on the make and model of the DSC equipment).
4. The analysis is initiated and the differential thermal analysis curve is recorded.

DSC Analysis Results:

Sample 1 (comparative) uses crystalline brinzolamide as obtained from the manufacturer; samples 2 is autoclaved brinzolamide; sample 3 contains a physical mixture of brinzolamide and Soluplus® in a ratio of 0.5:0.25 and sample 4 is according to the present invention (contains brinzolamide and Soluplus® in the ratio of 0.5:0.25) as shown in Table 1 and FIGS. 1 to 4.

TABLE 1

| Sr. No. | Remarks | Onset (° C.) | Peak (° C.) | Delta H (J/g) |
|---|---|---|---|---|
| 1 | API | 130.62 | 134.21 | 125.35 |
| 2 | API-autoclaved | 130.81 | 134.22 | 119.34 |
| 3 | Physical mixture of API:Soluplus ® (0.5:0.25) | 130.12 | 132.45 | 94.52 |
| 4 | API:Soluplus ® (0.5:0.25) | 121.82 | 127.28 | 8.213 |

Conclusion

DSC thermogram of API (brinzolamide) showed sharp endotherm at 134.21° C. corresponding to the melting point of drug exhibiting the crystalline nature of drug. Whereas the Soluplus® showed broad endothermic peak at 76.16° C. corresponding to the glass transition temperature of Soluplus® showing the amorphous nature of polymer. In physical mixture there is lowering of enthalpy of fusion (δH) which has further decreased significantly more in case of API: Soluplus® complex, indicating that less amount of energy is required to break its lattice while melting, confirming that crystallinity of API has decreased. This result further supports the amorphous/soluble nature imparted to API by Soluplus® which accounts for the improved solubilization of API.

Powder X-Ray Diffraction (PXRD):

X'Pert PRO, X-ray diffractometer system (Pananalytical, Netherlands) was used to get powder diffraction patterns of the samples using Cu as tube anode. The diffractograms were recorded under following conditions: voltage 45 kV, 40 mA, divergence slit 10 and angular range 5 and 50° in 2θ. The experimental PXRD patterns were refined using X'Pert High Score software.

XRD (X-ray diffraction) uses the total X-ray scattering of a compound to determine its crystallinity and no external standard is needed. In XRD spectra every crystalline substance gives a pattern; the same substance always gives the same pattern; and in a mixture of substances each produces its pattern independently of the others. The X-ray diffraction pattern of a pure substance is like a fingerprint of the substance. The powder diffraction method is thus ideally suited for characterization and identification of different crystalline phases. Therefore in present study we have used XRD (X-ray diffraction) as a tool to determine crystallinity of samples. It provides more accurate results and assuming that all data collection and processing variables are controlled. XRD (X-ray diffraction) provides very precise relative comparisons between samples as shown in Table 2.

TABLE 2

| S. No. | Formulation | Percentage Intensity (%) | |
|---|---|---|---|
| | | 12.4081 (2ø) | 16.3677 (2ø) |
| 1 | API* | 100 | 42.9 |
| 2 | Soluplus ®** | — | — |
| 3 | API:Soluplus ® physical mixture (0.5:0.25) | 100 | 40.36 |
| 4 | API:Soluplus ® (0.5:0.25) + PS*** 80(1%) | 100 | 18.58 |
| 5 | API:Soluplus ® physical mixture (0.5:0.375) | 100 | 46.24 |
| 6 | API:Soluplus ® (0.5:0.375) + PS 80(1%) | 84.22 | 14.03 |

*API is Brinzolamide.
**Soluplus ® is an amphiphilic polyvinyl caprolactam-polyvinyl acetate-polyethylene glycol graft copolymer (PVCap-PVAc-PEG).
***PS 80 is Polysorbate 80 (Polyoxyethylene (20) sorbitan monooleate).

Observation and Result:

A typical diffraction spectrum consists of a plot of reflected intensities versus the detector angle 2-THETA. In the process X-ray beam strikes at the fixed crystal plane and is diffracted. Therefore in the interpretation of XRD spectra the Position (2-THETA) value is used to identify the position of the peak with respect to the particular 2Θ value.

Maximum intensity (100% intensity) occurs when the beam of X-ray waves are in phase. In the present study at approx. 2Θ value of 12.4, peak at 100% intensity is appearing in all samples. Therefore, the inventors have compiled the data corresponding to this 2Θ angle.

Crystalline compounds will have planes going through higher electron density than the amorphous compounds therefore the corresponding intensities of the pure API are higher than the present invention formulation. Since a count represents the intensity, therefore the inventors of present invention formulation conclude that the counts of crystalline compounds are higher than the amorphous compounds.

Figure 1:
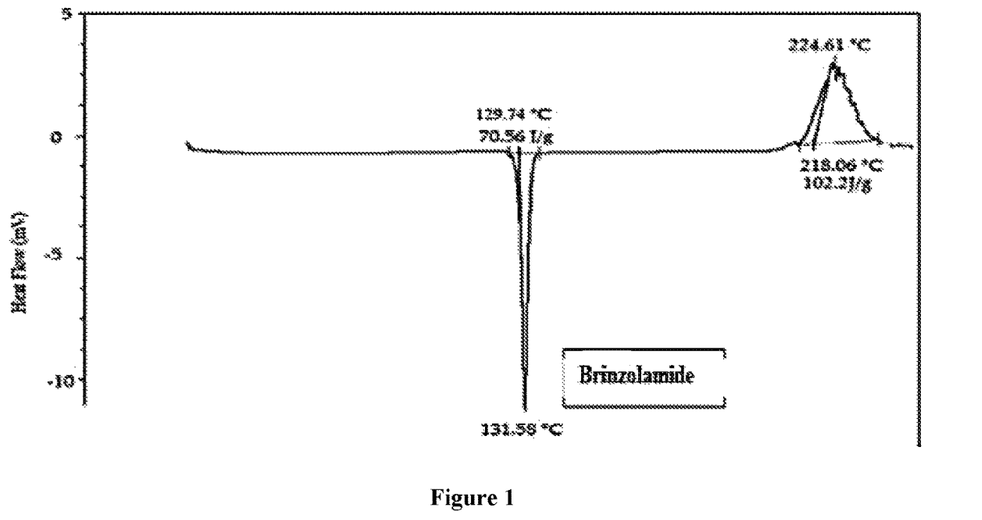
FIG. 1 is a DSC thermogram of pure APT (brinzolamide).
Figure 2:
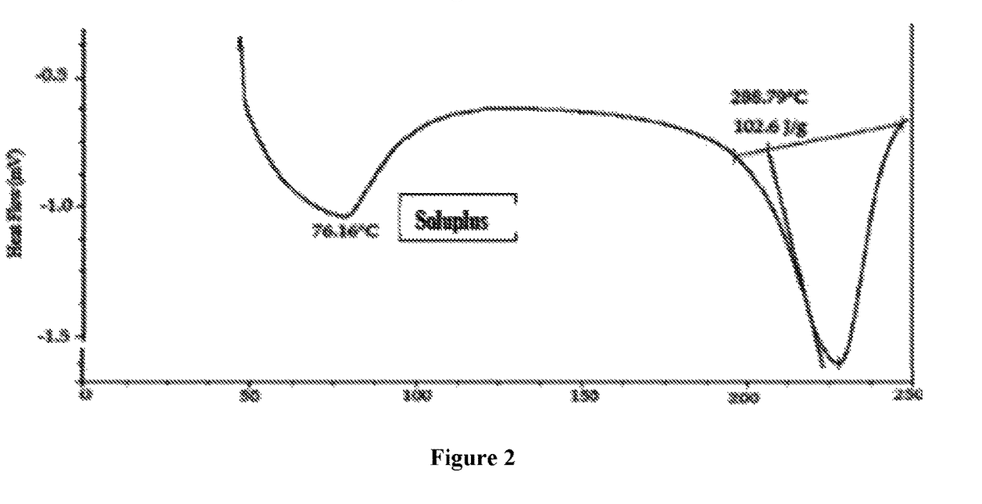
FIG. 2 is a DSC thermogram of pure Soluplus®.
Figure 3:
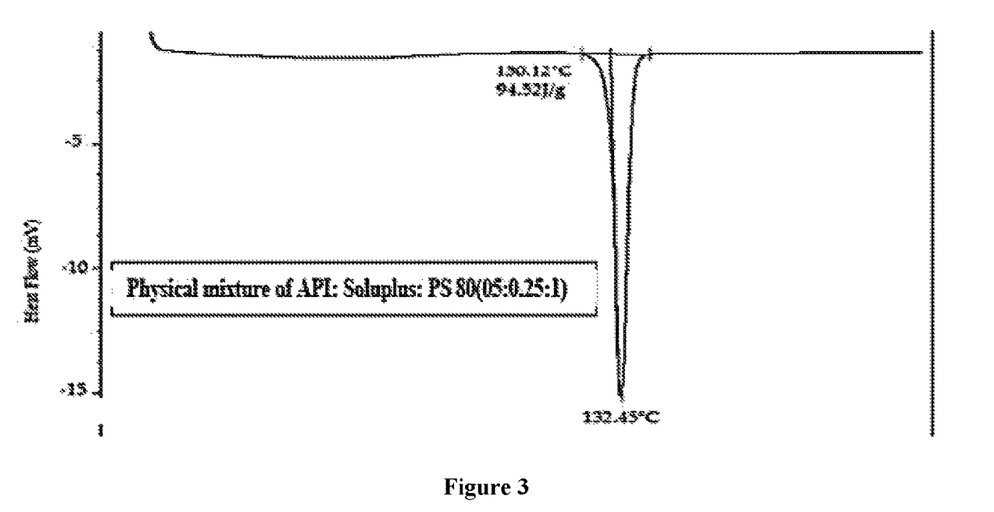
FIG. 3 is a DSC thermogram of formulation comprising API: Soluplus® physical mixture (0.5:0.25).
Figure 4:
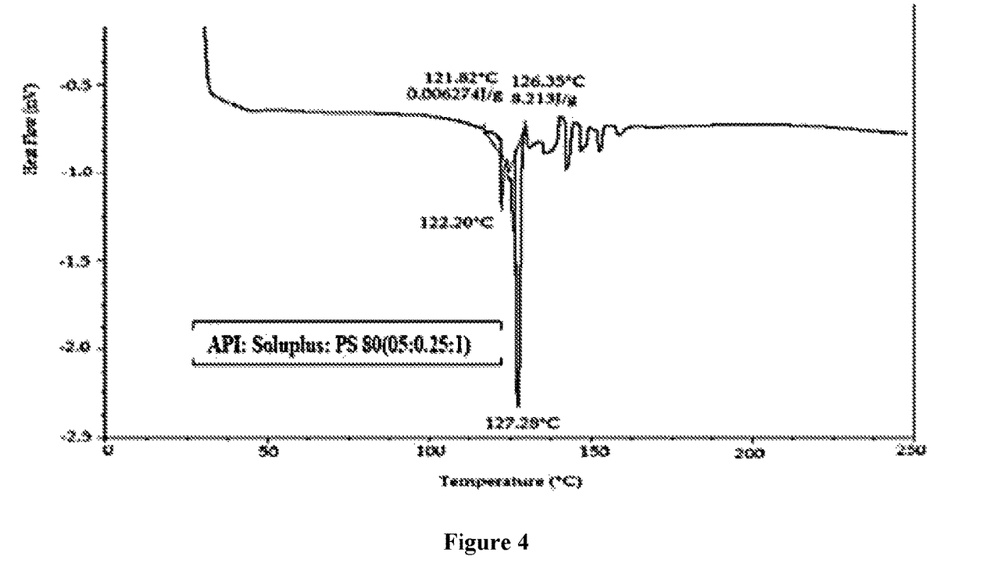
FIG. 4 is a DSC thermogram of formulation comprising API: Soluplus® (0.5:0.25)+PS 80 (1%).
Figure 5:
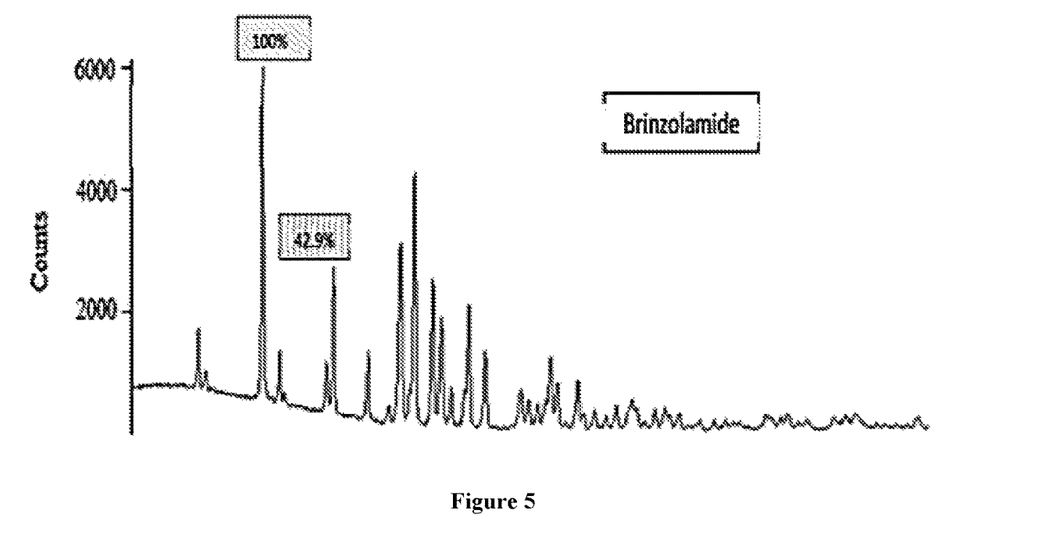
FIG. 5 is a diffractrogram of pure API (brinzolamide).
Figure 6:
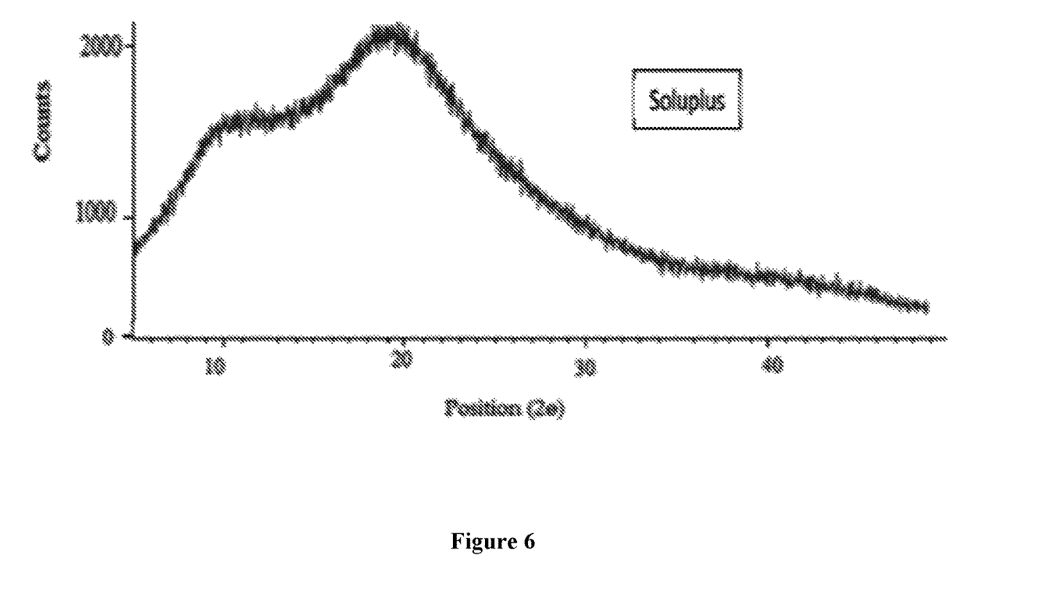
FIG. 6 is a diffractrogram of pure Soluplus®.
Figure 7:
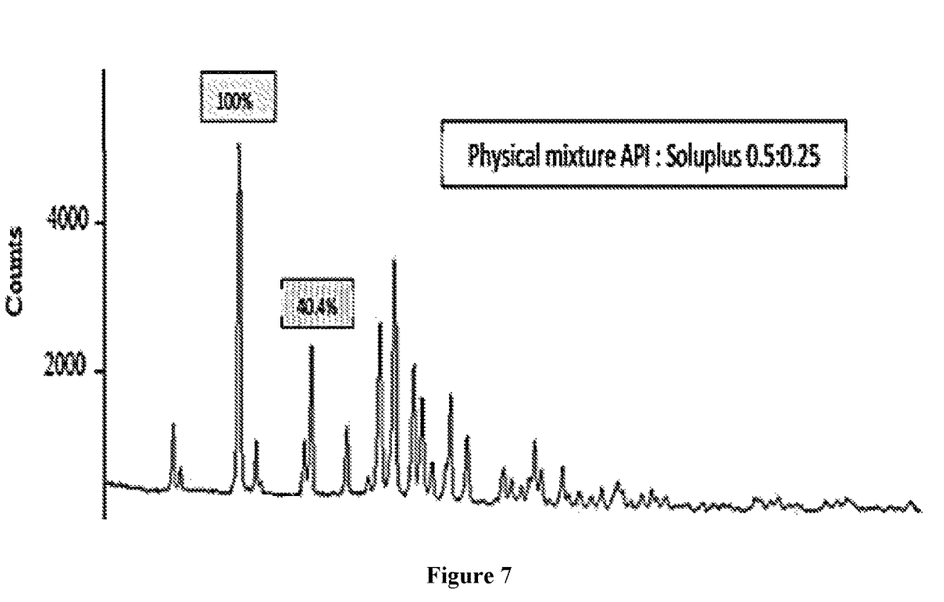
FIG. 7 is a diffractrogram of formulation comprising API: Soluplus® physical mixture (0.5:0.25).

In the present study it is observed that for the formulation comprising pure API, the counts lies in a range upto 6000 represents the crystalline nature of the API. For the formulation comprising pure Soluplus®, there is no prominent sharp peak instead showed a broad halo pattern and counts lies in a range upto 2000 represents the amorphous nature of the Soluplus®. For the formulation comprising pure API and Soluplus® physical mixture in the ratio of 0.5:0.25 respectively, the counts lies in a range upto 5000 represents the decrease in the crystalline nature of the API.

Figure 8:
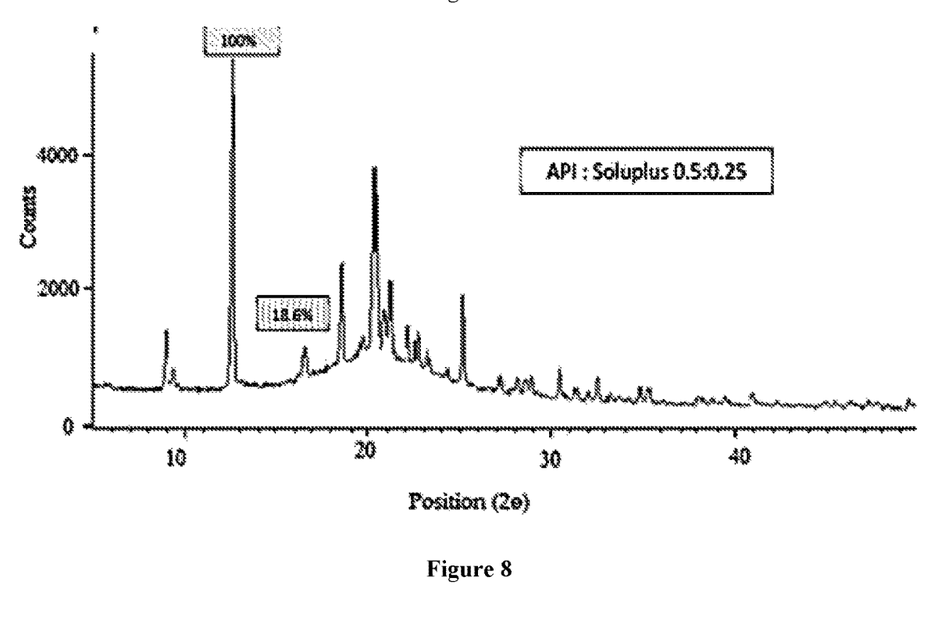
FIG. 8 is a diffractrogram of brinzolamide formulation comprising API: Soluplus® (0.5:0.25)+PS 80 (1%).

Further, for the formulation comprising API in combination with Soluplus® and polysorbate 80 in the ratio of 0.5:0.25:1 respectively, the counts lie in a range upto 6000 shows that 100% relative intensity peak is shifted to 13.06 from 12.4 as observed in pure API. Crystallinity of API has decreased as firstly, there is decrease in the relative intensity of prominent peaks as summarized in Table 3 and secondly, the peaks follows slightly halo pattern as was observed in case of Soluplus® indicating interaction of Soluplus® with API which has imparted amorphous nature to API.

TABLE 3

| | | Relative intensities | |
|---|---|---|---|
| Position | API | PHYSICAL MIXTURE (0.5:0.25) | API: SOLUPLUS (0.5:0.25) |
| 12.4 | 100 | 100 @ 12.39 | 100 @ 13.06 |
| 16.37 | 42.92 | 40.36 @ 16.36 | 18.58 @ 16.57 |

Figure 9:
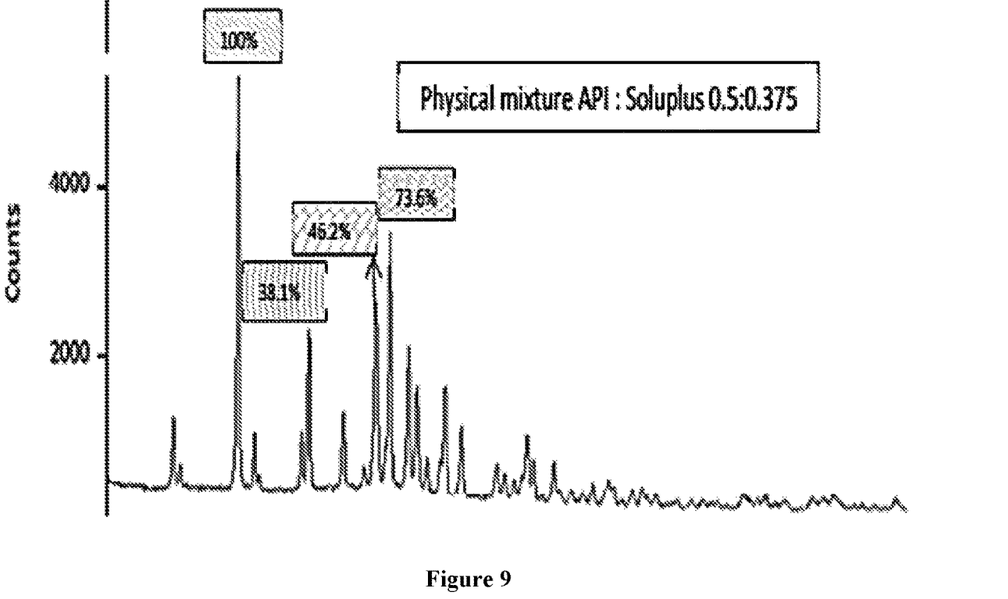
FIG. 9 is a diffractrogram of formulation comprising API: Soluplus® physical mixture (0.5:0.375).
Figure 10:
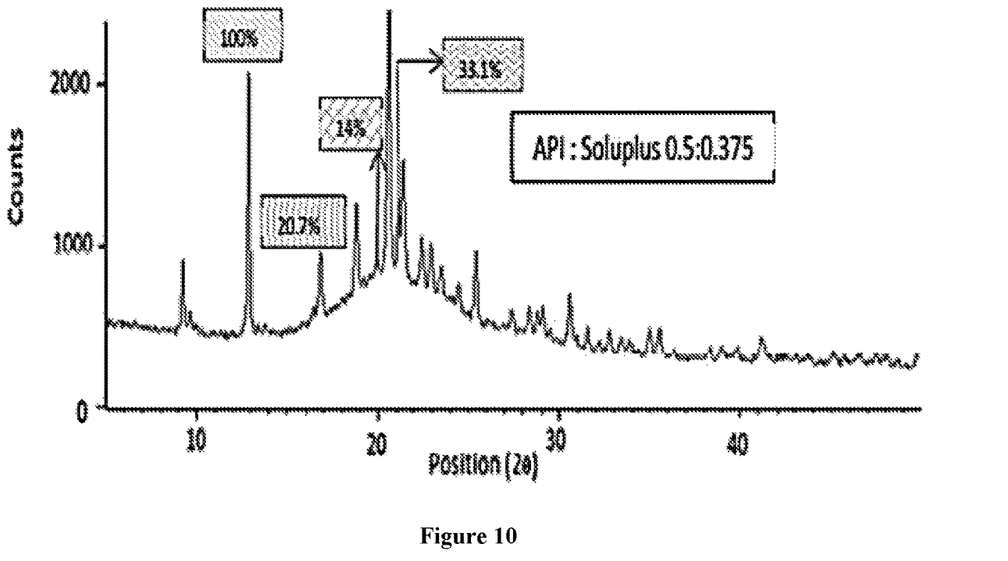
FIG. 10 is a diffractrogram of brinzolamide formulation co n API: Soluplus® (0.5:0.375)+PS 80 (1%).
Figure 11:
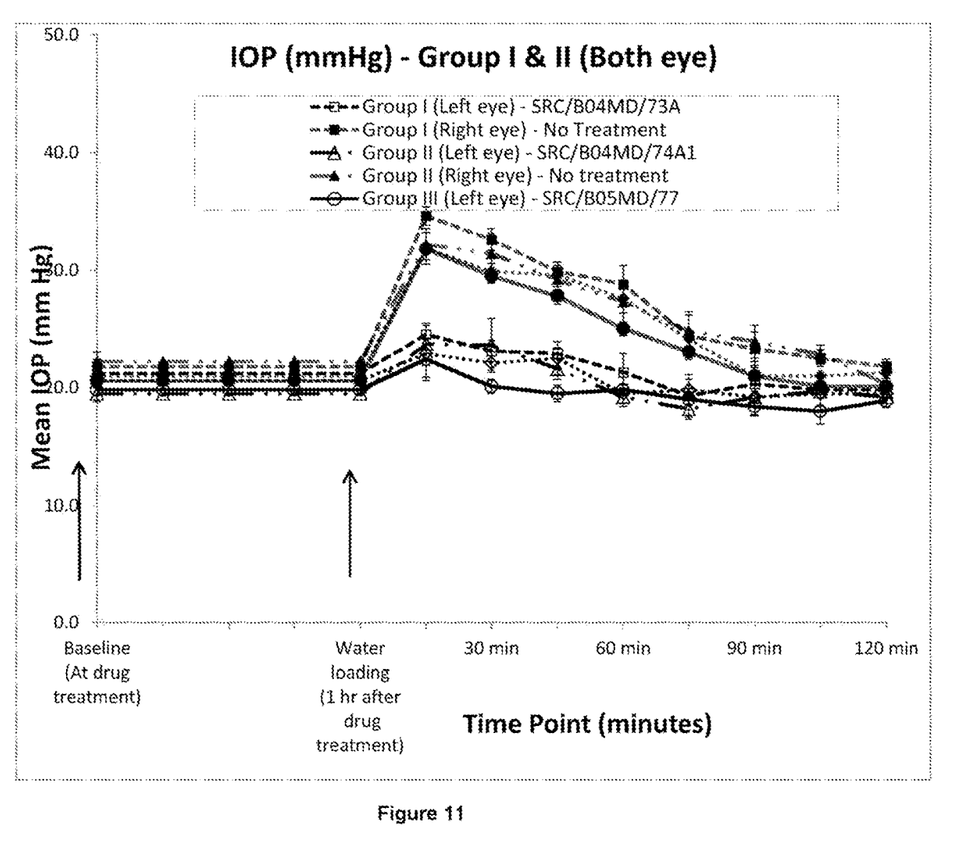
FIG. 11 is a comparative animal efficacy result of Group I, Group II, Group III and Group IV. Group I has API (0.4%)+Soluplus (0.4%), Group II has API (0.4%)+Soluplus (0.8%); Group III has API (0.5%)+Soluplus (0.4%); Group IV has API (1.0%), which is Azopt (reference listed drug).

Furthermore, for the formulation comprising pure API and Soluplus® physical mixture in the ratio of 0.5:0.375 respectively, the counts lies in a range upto 5000 represents the decrease in the crystalline nature of the API. But when the concentration of Soluplus® is increased from 0.25 to 0.375, there is sharp decrease in the counts and the count lays in a range upto 2500 shows that 100% relative intensity peak is shifted to 20.6 from 12.4 as observed in API. Crystallinity of API has decreased as firstly, there is change in the relative intensity of prominent peaks as summarized in Table 4 and secondly, the peaks follows slightly halo pattern as was observed in case of Soluplus® indicating interaction of Soluplus® with API which has imparted amorphous nature to API.

TABLE 4

| | | Relative intensities | |
|---|---|---|---|
| Position | API | PHYSICAL MIXTURE (0.5:0.375) | API: SOLUPLUS ® (0.5:0.375) |
| 12.4 | 100 | 100 @ 12.38 | 84.22 @ 12.90 |
| 16.37 | 42.92 | 38.15 @ 16.35 | 20.75 @ 16.83 |
| 20.13 | 52.86 @ 20.13 | 46.24 @ 20.11 | 14.03 @ 19.93 |
| | 73.59 @ 20.93 | 62.99 @ 20.9 | 33.1 @ 21.1O |

Conclusion

From the above data it is observed that in the formulation the percentage relative intensity of prominent peaks has decreased and the peaks follows a halo pattern indicating the transformation of API from crystalline to amorphous state which has led to increased solubilisation of API. This interpretation is further confirmed by DSC analysis.

Solubility Studies:

Procedure for Determining the Solubility of Brinzolamide:

Purified water was taken in Schott bottle. Brinzolamide was added with continuous stirring. After 30 min its pH was adjusted to 6. It was stirred for 24 hours. After which, the supernatant was filtered with 0.45 m syringe filter and then its solubility was determined.

Procedure for Determining the Solubility of Autoclaved Brinzolamide:

Purified water was taken in Schott bottle. Brinzolamide was added with continuous stirring. After 30 min its pH was adjusted to 6 and was autoclaved at 121° C./30 min. After autoclaving the sample was cooled to room temperature. It was stirred for 24 hours. After which, the supernatant was filtered with 0.45 m syringe filter and then its solubility was determined.

Procedure for Preparing the Present Invention Formulation:

Purified water is taken in Schott bottle. Soluplus® is added to it while stirring for 10-15 min. Polysorbate 80 is added to it while stirring for 10-20 min. After it has dissolved completely Brinzolamide is added with continuous stirring. After 30 min pH is checked and adjusted to 6 with 0.1 N NaOH. It is autoclaved at 121° C./30 min. After autoclaving the formulation is cooled to room temperature with stirring.

In order to determine the solubility the sample was centrifuged at 3500 rpm for 5 min followed by filtration through 0.45 m syringe filter and analysis.

Solubility Data:

Solubility of brinzolamide as per literature at pH 6.25 is 0.059% w/v and it was determined to be 0.0545% w/v at pH 6.0 in the lab. Interestingly, when API is autoclaved, and cooled, solubility comes out to be slightly higher, i.e., 0.082%, at pH 6.0. The solubility data are presented in Table 5, shown below.

TABLE 5

| Sr. No. | (Column 2) Composition for Determination of Solubility | Solubility % w/v | | |
|---|---|---|---|---|
| | | No Further addition to the ingredients of Column 2 | PEG 400 (5%) in addition to the composition of Column 2 | Polysorbate 80 (1%) in addition to the composition of Column 2 |
| 1 | Autoclaved API | 0.0822 | 0.0668 | 0.2089 |
| 2 | API:Soluplus® (1:0.1) | 0.228 | 0.2661 | 0.2414 |
| 3 | API:Soluplus® (1:0.25) | 0.3025 | 0.2966 | 0.3601 |
| 4 | API:Soluplus® (1:0.50) | 0.3232 | 0.3543 | 0.4807 |
| 5 | API:Soluplus® (1:0.75) | 0.4333 | 0.4226 | 0.4873 |
| 6 | API:Soluplus® (1:1) | ****ND | 0.2943 | 0.4694 |
| 7 | API:Soluplus® (1:3) | ND | 0.3483 | ND |
| 8 | API:Soluplus® (1:5) | ND | 0.4736 | ND |
| 11 | API:*Kolliphor TPGS (0.5:0.25) | 0.134 | ND | 0.207 |
| 12 | API:Kolliphor TPGS (0.5:0.375) | 0.134 | ND | 0.21 |
| 13 | API:Kolliphor TPGS (0.5:0.5) | 0.149 | ND | 0.221 |
| 14 | API:Kolliphor TPGS (0.5:1) | 0.176 | ND | 0.254 |
| 15 | API:Kollisolv (0.5:1.0) | ND | ND | 0.1065 |
| 16 | API:Solutol (0.5:1.0) | ND | ND | 0.1148 |
| 17 | API:PVP (1.0:1.0) | ND | ND | 0.1171 |
| 18 | API:PVA (1.0:1.0) | ND | ND | 0.1085 |
| 19 | API:**Brij C20 (0.5:1) | ND | ND | 0.1087 |
| 20 | API:Brij L23SO (0.5:1) | ND | ND | 0.1408 |
| 21 | API:***Brij S721 (0.5:0.25) | ND | ND | 0.0917 |
| 22 | API:Brij S721 (0.5:0.375) | 0.0653 | ND | 0.0961 |
| 23 | API:Brij S721 (0.5:0.5) | ND | ND | 0.1221 |
| 24 | API:Brij S721 (0.5:0.75) | ND | ND | 0.1022 |
| 25 | API:Brij S721 (0.5:1) | ND | ND | 0.1238 |
| 26 | API:Brij S721:Soluplus® (0.5:375:0.375) | 0.1727 | ND | 0.3264 |
| 27 | API:Acacia Gum (0.5:0.5) | ND | ND | 0.0961 |
| 28 | API:Acacia Gum (1:1) | ND | ND | 0.1266 |

*Kolliphor TPGS is D-alpha tocopheryl polyethylene glycol 1000 succinate.
**Brij C20 is Polyoxyethylene-(20)-cetyl alcohol.
***Brij S721 is Polyoxyethylene (21) stearyl ether.
****ND is Not Determined.

Based on the above data it is clear that polysorbate 80 helps to increase the solubility of brinzolamide from 0.085 to 0.2% w/v. PEG 400 also increases the solubility of brinzolamide however not as much as polysorbate 80.

The solubilized brinzolamide in an amorphous form is more liquid like and is having a greater bioavailability than the pure brinzolamide and due to this it is believed that formulations of the present invention have advantages over the prior marketed brinzolamide formulations.

It is believed and expected that material according to the present invention has higher permeability to ocular tissues than crystalline material, leading to higher bioavailability. It is believed that the disclosed present invention sterile, ophthalmic pharmaceutical formulation is superior to the formulations prepared in the prior art.

EXAMPLES

The present invention is further illustrated by reference to the following examples which is for illustrative purpose only and does not limit the scope of the invention in any way.

The term 'q.s.' wherever appears in the examples is an abbreviation for 'quantity sufficient' which is the amount of the excipient in such quantities that is just sufficient for its use in the composition of the present invention.

Example 1

| Ingredients | Quantity (% w/v) |
|---|---|
| Brinzolamide | 0.1-1.0 |
| Soluplus® | 0.1-2 |
| Polysorbate 80 | 0.5-2 |
| Carbomer 974P | 0.1-2.0 |
| Edetate disodium | 0.01-0.5 |
| Benzalkonium chloride | 0.002-0.01 |
| Mannitol | 1.0-5 |
| Sodium chloride | 0.1-0.5 |

| Ingredients | Quantity (% w/v) |
| --- | --- |
| Sodium Hydroxide | q.s |
| Hydrochloric Acid | q.s |
| Purified water | q.s |

Manufacturing Process:
The manufacturing process is divided into two parts:
Part I:
    Take 300 ml of water for injection in a beaker and add required quantity of polysorbate 80 and stir well. Then add required quantity of Soluplus® under continuous stirring. Weigh appropriate amount of brinzolamide and add to the beaker. Adjust pH of the mixture to 4.0 and continue stirring for 30 min. Then raise temperature of the mixture to 70° C. and maintain it for 30 min. After 30 min, cool the solution to room temperature. Sterile filter the solution into aseptic container.
Part II:
    In a suitable 1000 ml autoclavable Schott bottle, take 700 ml of water for injection. To that, add required quantity of Edetate disodium, Mannitol, Carbomer 974P, Sodium chloride and Benzalkonium chloride, one after the other, making sure that the previous ingredient is dissolved before adding the next one. After complete dissolution of all the ingredients, adjust the pH to 7.6. After adjusting the pH, viscosity of the solution will increase. Stir the solution for additional 30 min to ensure uniform mixing. Then autoclave the solution at 121° C. and 15 lbs of pressure for 30 min. After autoclaving, let the solution cool to room temperature. Once the solution is cooled to room temperature, aseptically add Part I to Part II, quantity sufficient it and stir it for 30 min. After homogenous mixing, pass the complete product through previously sterilized 20 filter.

Example 2

| Ingredients | Quantity (% w/v) |
| --- | --- |
| Brinzolamide | 0.40-0.50 |
| Soluplus | 0.4-0.8 |
| Polysorbate-80 | 1.0 |
| Tylaxapol | 0.025 |
| Edetate disodium | 0.01 |
| Mannitol | 3.3 |
| Carbomer | 0.45 |
| NaCl | 0.1-0.3 |
| Benzalkonium Chloride (50%) | 0.02 |
| NaOH | q.s. to adjust pH to 6.0 |
| HCl | q.s. to adjust pH to 6.0 |
| Milli Q | q.s. to 100 mL |

Manufacturing Process:
    The procedure is divided into four main steps:
    1. Preparation of Remaining Product Vehicle (RPV)
    2. Preparation of sterile Milli Q water
    3. Preparation of solution containing API
    4. Bulk preparation
1.0 Preparation of Remaining Product Vehicle (RPV)
    1) Take 60% (of actual batch size) of milli Q water in a clean glass beaker.
    2) Add slowly dispensed quantity of disodium edetate followed by mannitol under continuous stirring (rpm 800±100).
    3) Slowly add dispensed quantity of carbomer into the above solution at increased rpm (2000±100) via sprinkling. Decrease the stirring rate to 1200±100 after complete addition.
    4) After the carbomer has dissolved completely add dispensed quantity of sodium chloride followed by benzalkonium chloride under continuous stirring and stir till the solution is clear.
    5) Check the initial pH of the solution, and adjust the pH to 7.5 with 5 N sodium hydroxide solution.
    6) Make up the volume with milli Q water upto 80% (of actual batch size).
    7) Filter the bulk solution through 47 mm, 20 micron Polypropylene filters.
    8) Autoclave the RPV at 121° C. for 30 min in a Schott glass bottle.
Note: About 10% RPV excess is prepared to compensate the loss of RPV during filtration and autoclaving. Please note the formulation is stating the exact quantities. However, dispensed quantities will be in 10% excess.
2.0 Preparation of Sterile milli Q water
    1) In a Schott glass bottle autoclave enough water that will comprise 20% of total weight of the product. This can be autoclaved in a separate bottle, while autoclaving RPV. Autoclaving to be done at 121° C. for 30 min.
3.0 Preparation of Solution Containing API (Brinzolamide)
    1) Prepare 0.25% of tyloxapol solution in 200 mL beaker.
    2) Take 10% (of actual batch size) of 0.25% tyloxapol solution (if required in formulation, otherwise simply use water) added in a clean glass beaker.
    3) Add slowly dispensed quantity of Polysorbate 80 followed by soluplus to it under stirring.
    4) Add slowly dispensed quantity of API (brinzolamide) to it under continuous stirring.
    5) Decrease the pH of the slurry to approximately 3.5 with 5 N hydrochloric acid till the API dissolves completely.
    6) Filter through 47 mm, 0.45 micron PVDF filter followed by 47 mm, 0.22 micron PVDF filter into a large sterile container under laminar flow hood.
    7) Make up the volume of the solution to 20% of the bulk solution and adjust the pH of the solution to 6.0 with 5 N sodium hydroxide
4.0 Bulk Preparation
    1) To the above prepared sterile API solution which is 20% of the bulk solution, add previously autoclaved RPV to make up the weight to 90%. That is addition of about 70% of the RPV by weight.
    2) Make up the volume with previously sterilized milli Q water upto 100.0% (of actual batch size)
    3) Stir the solution for 2 hours in aseptic conditions.
    4) Fill the final solution in previously sterilized bottles, suitable for ophthalmic use.
Stability Data:
    Summarized below are the results of the physicochemical parameters on accelerated stability studies (40° C./NMT25% RH) conditions. The physical parameters evaluated are: Osmolality, pH and product description. The chemical parameters evaluated are concentration of Brinzolamide, its impurity profile, EDTA and benzalkonium chloride concentration.
    The stability results of the present invention are compared with innovator's marketed product brinzolamide ophthalmic suspension 1% (Azopt) and the comparison of concentration of brinzolamide and its impurity profile present in Table 1.
Effect of pH:
    Stability data (40° C./NMT25% RH) of two formulations whose final pH were adjusted at pH 6.0 and 7.5 respectively is summarized in Table 6.

TABLE 6

Accelerated stability data (40° C./NMT25% RH) of batches prepared at pH 6.0 and 7.5
40° C./NMT25% RH

| Parameters | Tentative specification | AZOPT (pH 7.5) | | | Present invention formulation (pH 6.0) | | | | Present Invention formulation (pH 7.5) | | | |
|---|---|---|---|---|---|---|---|---|---|---|---|---|
| | | Initial | 1 M | 3 M | Initial | 1 M | 2 M | 3 M | Initial | 1 M | 2 M | 3 M |
| Description | Not specified | White Suspension | | | White opalescent viscous solution | | | | White opalescent viscous solution | | | |
| Assay | 90%-110% w.r.t label claim | 98.58% | 100.20% | 100.70% | 97.00% | 98.30% | 99.00% | 98.80% | 98.80% | 100.50% | 100.80% | 99.80% |
| Imp A | NMT 1.5% | 0.91% | 0.96% | 1.39% | 0.04% | 0.37% | 0.62% | 0.93% | 0.04% | 0.48% | 0.85% | 1.19% |
| Imp B | NMT 0.5% | 0.05% | 0.05% | 0.04% | 0.06% | 0.12% | 0.12% | 0.12% | 0.06% | 0.11% | 0.13% | 0.13% |
| Imp D | Not specified | ND | ND | ND | ND | 0.02% | ND | 0.02% | ND | 0.01% | ND | ND |
| Any highest unknown imp | NMT 0.5% | 0.08% | 0.10% | 0.18% | 0.03% | 0.10% | 0.12% | 0.14% | 0.03% | 0.08% | 0.11% | 0.11% |
| Total impurity (except impurity A) | TBD | 0.12% | 0.15% | 0.35% | 0.15% | 0.38% | 0.47% | 0.67% | 0.15% | 0.30% | 0.36% | 0.44% |

ND: Not determined, NMT: Not more than, TBD: To be determined

Conclusion

From the above data it can be concluded that on accelerated stability conditions the impurities are increasing with time. However the rate of increase in impurity A is maximum as compared to the other impurities. Hence, it was critical to control it and keep it at same or lower level than innovator's product, AZOPT.

It is observed that the increase in impurity A at pH 6.0 is less than that observed at pH 7.5 (e.g. at 3 months, impurity A has increased to 0.93 from 0.12% in case of formulation at pH 6; whereas in case of formulation at pH 7.5 it has increased to 1.19 from 0.04% at same station). Hence pH 6.0 is better than pH 7.5, for keeping impurity A at lower level.

The impurity A of reference listed drug (AZOPT) is comparable with that observed in the formulation at pH 6.0. (e.g. at 3 months, impurity A has increased to 0.96 in case of AZOPT and 0.93% in case of present invention formulation at pH 6). However, it is interesting to note that the impurity A at initial time point is much higher in case of AZOPT (0.91%) than compared with present invention formulation at pH 6 (0.12). From the above observations it can be concluded that optimum pH for preparing the formulation is 6.0.

Effect of Heat During Preparation:

Two batches were prepared to compare the effect of heat during preparation of API slurry. One batch was prepared without involving heating via following the procedure as mentioned above. However another batch was prepared with similar process but heating the API slurry for 10-15 min at 70±5° C. (the transition temperature of the polymer) before reducing the pH of API slurry to approximately 4.0 so that it can be filtered. These formulations were then charged on accelerated stability conditions and their results are compiled in Table 7.

TABLE 7

Accelerated stability data (40° C./NMT25% RH) of batches prepared with and without heating
40° C./NMT25% RH

| Parameters | Tentative specification | Present invention formulation (prepared without heating) (pH 6.0) | | | | Present Invention formulation (prepared with heating) (pH 6.0) | | | |
|---|---|---|---|---|---|---|---|---|---|
| | | Initial | 1 M | 2 M | 3 M | Initial | 1 M | 2 M | 3 M |
| Description | Not specified | White opalescent viscous solution | | | | White opalescent viscous solution | | | |
| Assay | 90%-110% w.r.t label claim | 97.00% | 98.30% | 99.00% | 98.80% | 98.80% | 100.80% | 100.50% | 100.30% |
| Imp A | NMT 1.5% | 0.04% | 0.37% | 0.62% | 0.93% | 0.04% | 0.37% | 0.64% | 0.98% |
| Imp B | NMT 0.5% | 0.06% | 0.12% | 0.12% | 0.12% | 0.07% | 0.13% | 0.13% | 0.13% |
| Imp D | Not specified | ND | 0.02% | ND | 0.02% | ND | 0.01% | ND | 0.01% |
| Any highest unknown imp | NMT 0.5% | 0.03% | 0.10% | 0.12% | 0.14% | 0.08% | 0.11% | 0.13% | 0.15% |
| Total impurity (except impurity A) | TBD | 0.15% | 0.38% | 0.47% | 0.67% | 0.28% | 0.39% | 0.46% | 0.69% |

ND: Not determined, NMT: Not more than, TBD: To be determined

Conclusion

The above data indicates that there is no significant change in assay and impurity of the two batches prepared with and without heating, on charging them at 40° C./NMT25% RH.

Effect of Temperature on the Stability of the Formulation:

In order to study the impact of temperature on the stability of final formulation same batch was charged on stress (50° C.) and accelerated stability conditions (40° C./NMT25% RH). The results of the study are summarized in Table 8.

TABLE 8

Stress and accelerated stability data of same batch

| Parameters | Tentative specification | AZOPT (charged on 40° C./NMT25% RH) | | | Present invention formulation (charged on 40° C./NMT25% RH) (pH 6.0) | | | | | Present Invention formulation (charged on 50°C.) (pH 6.0) | | |
|---|---|---|---|---|---|---|---|---|---|---|---|---|
| | | Initial | 1 M | 3 M | Initial | 2 W | 1 M | 2 M | 3 M | Initial | 2 W | 4 W |
| Description | Not specified | White Suspension | | | White opalescent viscous solution | | | | | White opalescent viscous solution | | |
| Assay | 90%-110% w.r.t label claim | 98.58% | 100.20% | 100.70% | 97.00% | 98.00% | 98.30% | 99.00% | 98.80% | 97.00% | 96.80% | 99.30% |
| Imp A | NMT 1.5% | 0.91% | 0.96% | 1.39% | 0.04% | 0.16% | 0.37% | 0.62% | 0.93% | 0.04% | 0.60% | 1.03% |
| Imp B | NMT 0.5% | 0.05% | 0.05% | 0.04% | 0.06% | 0.08% | 0.12% | 0.12% | 0.12% | 0.06% | 0.05% | 0.16% |
| Imp D | Not specified | ND | ND | ND | ND | ND | 0.02% | ND | 0.02% | ND | ND | ND |
| Any highest unknown imp | NMT 0.5% | 0.08% | 0.10% | 0.18% | 0.03% | 0.04% | 0.10% | 0.12% | 0.14% | 0.03% | 0.04% | 0.12% |
| Total impurity (except impurity A) | TBD | 0.12% | 0.15% | 0.35% | 0.15% | 0.21% | 0.38% | 0.47% | 0.67% | 0.15% | 0.13% | 0.38% |

ND: Not determined, NMT: Not more than, TBD: To be determined

Conclusion

From the above data it can be concluded that the impurity A and B are increasing with time and the increase is at higher rate at higher temperature. Temperature has higher impact on impurity A than impurity B. The impurity A at initial time point is more in case of RLD than present invention formulation. Even though the impurities are increasing they are well within the specification after 3 months at 40° C./NMT25% RH and are comparable with the RLD.

Effect of Increase in Soluplus® Concentration:

In order to study the impact of increase in concentration of polymer (Soluplus®), it was observed that the Soluplus® concentration was increased from 0.4% to 0.8% and was compared with normal batch as indicated in Table 9.

Animal Efficacy Studies:

A study was conducted to compare the animal efficacy of the present invention formulations with the commercial product (AZOPT) and the Intra ocular pressure (IOP) of the eye is measured. The details of the batches are:

| Group | Batch No. | Description |
|---|---|---|
| Group I | SRC/B04MD/73A | API (0.4%) + Soluplus ® (0.4%) |
| Group II | SRC/B04MD/74A1 | API (0.4%) + Soluplus ® (0.8%) |
| Group III | SRC/B05MD/77 | API (0.5%) + Soluplus ® (0.4%) |
| Group IV | SRC/B1MD/231374F | API (1%) – Azopt (RLD) |

TABLE 9

Comparative stability data of batch with optimum and double Soluplus ® concentration 40° C./NMT25% RH

| Parameters | Tentative specification | AZOPT (pH 7.5) | | | Present invention formulation Soluplus ® concentration (pH 6.0) | | | | Present Invention formulation (with 0.8% Soluplus ® concentration) (pH 6.0) | | | |
|---|---|---|---|---|---|---|---|---|---|---|---|---|
| | | Initial | 1 M | 3 M | Initial | 1 M | 2 M | 3 M | Initial | 1 M | 2 M | 3 M |
| Description | Not specified | White Suspension | | | White opalescent viscous solution | | | | White opalescent viscous solution | | | |
| Assay | 90%-110% w.r.t label claim | 98.58% | 100.20% | 100.70% | 97.00% | 98.30% | 99.00% | 98.80% | 96.30% | 97.30% | 98.30% | 99.00% |
| Imp A | NMT 1.5% | 0.91% | 0.96% | 1.39% | 0.04% | 0.37% | 0.62% | 0.93% | 0.04% | 0.30% | 0.49% | 0.56% |
| Imp B | NMT 0.5% | 0.05% | 0.05% | 0.04% | 0.06% | 0.12% | 0.12% | 0.12% | 0.08% | 0.14% | 0.15% | 0.15% |
| Imp D | Not specified | ND | ND | ND | ND | 0.02% | ND | 0.02% | ND | 0.01% | ND | 0.01% |
| Any highest unknown imp | NMT 0.5% | 0.08% | 0.10% | 0.18% | 0.03% | 0.10% | 0.12% | 0.14% | 0.03% | 0.11% | 0.09% | 0.15% |
| Total impurity (except impurity A) | TBD | 0.12% | 0.15% | 0.35% | 0.15% | 0.38% | 0.47% | 0.67% | 0.20% | 0.41% | 0.41% | 0.77% |

ND: Not determined, NMT: Not more than, TBD: To be determined

Conclusion

Following inferences can be drawn from above data, with the increase in conc. of soluplus the impurity A decreases (At 3 months the impurity A is 0.93% at Soluplus® concentration of 0.4% and 0.56% with double Soluplus® concentration of 0.8%). Hence, Soluplus® has stabilizing effect on brinzolamide.

Intra Ocular Pressure (IOP) Measurement:

On first day, initially baseline IOP was measured and then rabbits were administered with water @ 70 mL/kg through orogastric tube and IOP was measured till the baseline IOP achieved (for 2 hrs) at 0.25 hr interval to observe the IOP pattern. Statistically significant ($p<0.05$) increased intraocular pressure was observed from 15 min to 60 min in left eye and 15 min to 75 min in right eye of rabbits from Group I, from 15 min to 60 min in both eyes of rabbits from Group II, from 15 min to 60 min in left eye and 15 min to 90 min in right eye of rabbits from Group III & from 15 min to 60 min in left eye and 15 min to 75 min in right eye of rabbits from Group IV as compare to its baseline reading.

At the same time, when within the group left eyes were compared with right eyes, it showed comparable increase in IOP and no statistically significant (p<0.05) changes in IOP was observed for all dose groups. Same way when left and right eyes of different groups compared with left and right eyes of other groups, there were no statistically significant (p<0.05) changes observed in IOP.

On the next day, test items were instilled in left eye of respective groups after baseline IOP measurement. One hour after test item instillation, animal were orally dosed rapidly with 70 mL/kg of water. This time gap was derived from time to peak intraocular pressure lowering effect of the drug observed in normotensive rabbit study numbered 142099 which was 1-3 hrs and the time of peak IOP elevation observed in water loaded untreated animal (15 min-90 min) in this study numbered 142100.

As compared to baseline, there was statistically significant (p<0.05) increase in IOP at 15 to 60 min in right eye of Groups I to III and at 15 to 75 min in right eye of Group IV. Left eyes (treated eyes) of all dose groups, did not reveal statistically significant (p<0.05) changes as compared to baseline.

At the same time, when both left and right eyes were compared, there was statistically significant (p<0.05) lower IOP observed in left eyes as compare to right eyes from 15 min to 75 75 min in Groups I & IV and from 15 min to 60 min in Groups II & TR. Left eyes of group I revealed statistically significant (p<0.05) lower IOP as compared to right eyes 105 & 120 min also. This change was observed after reaching baseline at 90 min and hence considered as biological variation.

In the same way when left and right eyes of different groups were compared with left and right eyes of other, there were no statistically significant (p<0.05) changes observed in IOP, except significant (p<0.05) slight higher IOP observed at 30 minute in left eyes of Group I as compared to left eyes of Group III as well as slight higher IOP in left eyes of group IV at 45 min as compared to left eyes of group III. This difference might be due to difference in baseline of left eyes of respective groups and considered as biological variation.

All the test groups revealed IOP reducing effect as compared to untreated eyes. At the same time, left eyes (treated eyes) of all the treated dose groups showed no significant difference in intra ocular pressure increase as compared to baseline IOP whereas right eyes (control eyes) showed statistically significant difference at different time points as compared to baseline IOP. SRS/B05MD/77 showed slightly more reduction in IOP levels at 30 min and 45 min time points as compared to other formulations but the reduction was not statistically significant hence not considered as different than other formulations.

Based on the observations obtained from present study, it is concluded that the present four formulations SRC/B04MD/73A, SRC/B04MD/74A1, SRC/B05MD/77 and SRC/B1MD/231374F have statistically significant IOP lowering efficacy and are comparable to each other.

CONCLUSION

Based on the observations obtained from this study, it is concluded that the different present invention formulations SRC/B04MD/73A, SRC/B04MD/74A1, SRC/B05MD/77 and commercially available formulation SRC/B1MD/231374F showed statistically significant IOP lowering efficacy when administered to water loaded New Zealand white rabbits by ocular route.

The onset of statistically significant IOP lowering efficacy was almost similar in all formulations, where all formulations were found to be comparable at each time point observed, which concludes that the IOP lowering efficacy of all test formulations (SRC/B04MD/73A, SRC/B04MD/74A1, SRC/B05MD/77 and SRC/B1MD/231374F) were statistically comparable.

UTILITY OF THE PRESENT INVENTION

The present inventors provide a sterile, ophthalmic pharmaceutical formulation comprising Carbonic anhydrase inhibitors and/or, pharmaceutically acceptable excipients wherein, the active ingredient with low aqueous solubility solubilizes, either during cooling after autoclaving or cooling after heating above 50° C., in either an amorphous form or in solution form resulting in improved bioavailability and manufacturability. Further, the process of preparing the formulation is simpler, cost effective, efficient and do not require equipment's such as ball mill and/or, jet mill. Furthermore, the prepared formulation is useful in treatment of elevated intraocular pressure.

The invention claimed is:

1. An aqueous ophthalmic pharmaceutical formulation formed by combining at least:
   a) water,
   b) brinzolamide,
   c) polyvinyl caprolactam-polyvinyl acetate-polyethylene glycol graft copolymer, and
   d) a surfactant,
   under time, temperature and pH conditions to convert the brinzolamide into a dissolved form and/or a soluble complex, and the formulation is a solution.

2. The formulation according to claim 1, wherein the brinzolamide is combined in an amount from 0.1% to 1% w/v.

3. The formulation according to claim 1, wherein the polyvinyl caprolactam-polyvinyl acetate-polyethylene glycol graft copolymer is combined in an amount from 0.1% to 1.5% w/v.

4. The formulation according to claim 3, wherein the polyvinyl caprolactam-polyvinyl acetate-polyethylene glycol graft copolymer is combined in an amount of less than 1% w/v.

5. The formulation according to claim 1, wherein the surfactant comprises sodium lauryl sulfate, docusate sodium, polyoxyalkyl ether, polyoxylalkyl phenyl ether, polyoxyl 40 hydrogenated castor oil, polyoxyl 40 stearate, polyoxy hydrogenated castor oil, polyoxy sorbitan ester, sorbitan ester, polysorbate, polyoxyl 35 castor oil, sorbitan monolaureate, poloxamer, or a combination of two or more thereof.

6. The formulation according to claim 5, wherein the surfactant is a polysorbate.

7. The formulation according to claim 6, wherein the polysorbate is polysorbate 80.

8. The formulation according to claim 7, wherein the surfactant is combined in an amount from 0.1% to 2.0% w/v.

9. The formulation according to claim 1, wherein the formulation further comprises a pharmaceutically acceptable excipients comprising a preservative, a chelating agent, buffers, an osmotic agent, a tonicity agent, pH adjusting agent(s), viscosity enhancing agent(s), a non-aqueous solvent, an antioxidant, or a combination of two or more thereof.

10. The formulation according to claim 1, wherein the formulation is formed by combining at least brinzolamide, polyvinyl caprolactam-polyvinyl acetate-polyethylene glycol graft copolymer, and polysorbate 80.

11. A process of preparing an aqueous ophthalmic pharmaceutical formulation, comprising preparing a composition by combining brinzolamide, polyvinyl caprolactam-polyvinyl acetate-polyethylene glycol graft copolymer, a surfactant and water under time, temperature and pH conditions to convert the brinzolamide into a dissolved form and/or a soluble complex wherein the formulation is a solution.

12. The process according to claim 11, wherein the brinzolamide does not precipitate in crystalline form during the cooling of the composition.

13. A method of treating elevated intraocular pressure in a patient in need thereof, comprising administering an effective amount to treat elevated intraocular pressure of the formulation according to claim 1 to at least one eye in need thereof of the patient.

14. The method according to claim 13, wherein the formulation is administered once a day to the at least one eye in need thereof after a loading dose of twice a day for a period of time not exceeding 3 months.

15. The method according to claim 13, wherein the formulation is administered twice a day to the at least one eye in need thereof, instead of normal dosing of three times a day.

16. A method of treating elevated intraocular pressure in a patient in need thereof, comprising administering an effective amount to treat elevated intraocular pressure of the formulation according to claim 2 to at least one eye in need thereof of the patient.

17. An aqueous ophthalmic pharmaceutical formulation comprising a brinzolamide complex formed from an aqueous composition containing brinzolamide and polyvinyl caprolactam-polyvinyl acetate-polyethylene glycol graft copolymer, the brinzolamide complex having a crystallinity that is lower than the crystallinity of crystalline brinzolamide in brinzolamide 1% suspension.

18. The formulation according to claim 17, wherein the aqueous composition additionally comprises a surfactant.

19. The formulation according to claim 17, wherein the brinzolamide is included in the composition in an amount from 0.1% to 1% w/v.

20. The formulation according to claim 17, wherein the polyvinyl caprolactam-polyvinyl acetate-polyethylene glycol graft copolymer is included in the composition in an amount from 0.1% to 1.5% w/v.

21. The formulation according to claim 18, wherein the surfactant is a polysorbate.

22. The formulation according to claim 21, wherein the polysorbate is polysorbate 80.

23. An aqueous ophthalmic pharmaceutical formulation formed by combining at least:
   a) water,
   b) brinzolamide in an amount from 0.1% to 1% w/v,
   c) polyvinyl caprolactam-polyvinyl acetate-polyethylene glycol graft copolymer in an amount from 0.1% to 1.5% w/v, and
   d) a surfactant in an amount from 0.1% to 2.0% w/v;
   wherein crystallinity of brinzolamide in the formulation is less than crystallinity of crystalline brinzolamide in brinzolamide 1% suspension.

24. The formulation of claim 23 wherein the crystallinity of brinzolamide in the formulation is less than the crystallinity of crystalline brinzolamide based on X-ray diffraction.

25. The formulation of claim 23 wherein the crystallinity of brinzolamide in the formulation is less than the crystallinity of crystalline brinzolamide based on differential scanning calorimetry.

* * * * *